United States Patent [19]

Morita et al.

[11] Patent Number: 4,929,378

[45] Date of Patent: May 29, 1990

[54] BATH PREPARATION

[75] Inventors: Yasuhiko Morita, Kyoto; Yoshitomi Kakiguchi, Osaka; Seiji Izuhara, Tondabayashi, all of Japan

[73] Assignee: Takeda Chemical Industries, Ltd., Osaka, Japan

[21] Appl. No.: 352,680

[22] Filed: May 10, 1989

Related U.S. Application Data

[63] Continuation of Ser. No. 63,916, Jun. 19, 1987, abandoned.

[30] Foreign Application Priority Data

Jul. 3, 1986 [JP] Japan .................. 61-156697

[51] Int. Cl.$^5$ .................. C11D 7/32; D06L 3/10
[52] U.S. Cl. .................. 252/105; 252/117; 252/121; 252/96; 252/399; 134/42; 134/2; 424/663
[58] Field of Search .................. 252/105, 96, 174.23, 252/399, DIG. 5, DIG. 13, 94

[56] References Cited

U.S. PATENT DOCUMENTS

| | | | |
|---|---|---|---|
| 2,694,719 | 11/1954 | Opplt | 514/474 |
| 4,295,985 | 10/1981 | Petrow | 252/105 |

FOREIGN PATENT DOCUMENTS

| | | |
|---|---|---|
| 2062249 | 6/1971 | France . |
| 6283 | of 1984 | Japan . |
| 215612 | of 1985 | Japan . |
| 0215613 | 4/1985 | Japan . |
| 0234411 | 10/1985 | Japan . |
| 96410 | of 1987 | Japan . |

Primary Examiner—Paul Lieberman
Assistant Examiner—John F. McNally
Attorney, Agent, or Firm—Wegner & Bretschneider

[57] ABSTRACT

The bath preparation of the present invention comprises an ascorbic acid compound and at least one reducing agent selected from the group consisting of water-soluble thiosulfate, water-soluble dithionite, L-cysteine hydrochloride, glutathione and gallic acid ester.

3 Claims, No Drawings

BATH PREPARATION

This application is a continuation of U.S. application Ser. No. 063,916, filed June 19, 1987 now abandoned.

The present invention relates to a bath preparation containing ascorbic acid or a derivative thereof and a reducing agent.

The azo dye Yellow No. 4, quinoline dye Yellow No. 203, natural dye betanin, etc. which are generally used as bath colors are mostly oxidized and discolored by residual free chlorine in tap water, and ascorbic acid has heretofore been used as a stabilizer for such dyes (Japanese Unexamined Laid-open No.53-27770).

There has been the problem that at a low concentration provided by the addition of such a bath preparation as above to bath water, ascorbic acid is rapidly decomposed and mostly oxidized to dehydroascorbic acid by residual free chlorine in tap water.

The present inventors conducted intensive research to develop an ascorbic acid-containing bath preparation wherein the ascorbic acid can be maintained in the stable condition in the bath water and found that the addition of a member of the group consisting of sodium thiosulfate, sodium dithionite, L-cysteine hydrochloride, glutathione and propyl gallate, all of which are selected from among known compounds, to bath water helps stabilize not only the ascorbic acid but also the colors in the bath water. The present invention has been accomplished on the basis of the above finding.

The present invention is therefore directed to a bath preparation comprising ascorbic acid, its ester or their water-soluble salt and at least one reducing agent selected from the group consisting of water-soluble thiosulfate, water-soluble dithionite, L-cysteine hydrochloride, glutathione and gallic acid ester.

As examples of the ascorbic acid ester which is used in the present invention, there may be mentioned ascorbic acid-2-phosphate, ascorbic acid-2-sulfate, and so on. As examples of the water-soluble salt of the ascorbic acid or its ester, there may be mentioned alkali metal or alkali earth metal ascorbates, such as sodium ascorbate, calcium ascorbate, sodium ascorbic acid-2-phosphate, calcium ascorbic acid-2-phosphate, magnesium ascorbic acid-2-phosphate, barium ascorbic acid-2-sulfate, and so on.

In the following description, these compounds will sometimes be referred to collectively as "ascorbic acid compound".

As the ascorbic acid compound, ascorbic acid or sodium ascorbate is preferably used.

As examples of the water-soluble thiosulfate which is used in the present invention, there may be mentioned alkali metal, such as sodium thiosulfate, potassium thiosulfate, and so on, sodium thiosulfate is preferably used.

As examples of the water-soluble dithionite, there may be mentioned alkali metal dithionites, such as sodium dithionite, potassium dithionite, and so on, sodium dithionite is preferably used. The gallic acid ester has an alkyl moiety having 1 to 4 carbons, propyl gallate is preferably used.

The bath preparation according to the present invention can be manufactured by blending said ascorbic acid or a derivative thereof with at least one member of said reducing agents. As to the blending ratio of the two components, the reducing agent is used generally in a proportion of 0.02 to 2 weight parts and preferably in a range of 0.05 to 0.5 weight part to each one weight part of the ascorbic acid compound. With regard to the amounts incorporated in the bath preparation, it is preferable to incorporate about 5 to 50 weight parts of said ascorbic acid compound and about 1 to 10 weight parts of said reducing agent to each 100 weight parts of the bath preparation.

The bath preparation according to the present invention may be provided in any suitable application forms such as solid tablets (for example, cubes, pills, foaming tablets, etc.), granules and powders as well as solutions and other liquids.

Further, the bath preparation according to the present invention may contain any of the bath components which are commonly employed, such as inorganic substances, essential oils, crude drugs, oils, perfumes, colors, soap, surfactants and so on.

As examples of said inorganic materials, there may be mentioned sodium chloride, potassium iodide, ammonium chloride, sodium sulfate, aluminum sulfate, iron sulfate, potassium sulfide, potassium nitrate, sodium bicarbonate, sodium carbonate, sodium sesquicarbonate, magnesium carbonate, magnesium bicarbonate, borax, boric acid, anhydrous silicic acid, metasilicic acid, sodium polyphosphate, dibasic calcium phosphate, sodium phosphate, calcium oxide, iron subsulfide, calcium hydroxide, neutral clay, perlite, sulfur, mica powder, mineral spring, mineral sand, incrustations of hot-spring water, and so on.

As examples of said essential oils, there may be mentioned peppermint oil, jasmine, artificial musk, camphor, camphor oil, hinoki oil, orange peel oil, borneol, terpene oil, cinnamon oil, bergamot oil, mandarin orange, iris oil, pine oil, lavender oil, pei oil, orange oil, cinnamon oil, cidar oil, clove oil, hiba oil, rose oil, eucalyptus oil, lemon oil and so on.

Examples of said crude drugs include soozyutu (*Atractylodis rhizoma*), byakuzyutu (*Atractylodis album rhizoma*), valerianae rhizoma, keigai (*Nepetae herba*), kooboku (*Magnoliae cortex*), senkyuu [*Cnidii rhizoma* (cnidium rhizome)], toohi [*Aurantii pericarpium* (bitter orange peel)], ninzin (*Ginseng radix*), keihi [*Cinnamomi cortex* (cinnamon bark, cassia bark)], syakuyaku (*Paeoniae radix*), *Menthae folium*, oogon (*Scutellariae radix*), bukuryoo (Hoelen), syoobukon (*Calami rhizoma*), syootoo (*Schizandrae lionum*), byakusi (*Angelicae radix*), safron (*Croci stigma*), oobaku (*Phellodendrae cortex*), uikyoo (*Foeniculi fructus*), Tinpi (*Aurantii nobilis pericarpium*), ganpi, chamomile (*Chamomillae flos*), radish (*Raphani rhizoma*), salix, syooboku (*Camphorae lionum*), sekkotubokuyoo (*Sambuci japonicae folium*), sokutyoo (*Sambuci folium*), koodyu (*Elsholtiae herba*), Fatsia japonica, sekisyoo (*Acori graminei rhizoma*), guiyoo (*Artemisiae folium*), syoorengyoo (*Hyperici herba*), orange pease, toohi (*Aurantii pericarpium*), peach drupe (*Pruni persicae semen*) and peach blossom (*Pruni persicae flos*), sookyoo (*Gleditschiae fructus*), biwanin (*Eriobotryae semem*) and biwayoo (*Eriobotryae folium*), nindoo (*Lonicerae folium*), byakusi (*Anoelicae radix*), limetree flower (Lindenflower), horse chestnut, *Achilleae sibirica herba*, hops, rosemary (*Rosmarini folium*), birch, pine (Pinus), yarenzura, lantana (red sage), kanzoo (*Liguiritiae radix*), *Valerianae rhizoma*, and so on.

Examples of said oils include olive oil, soybean oil, almond oil, peanut oil, castor oil, coconut oil, palm oil, turtle oil, rice bran oil and so on.

Examples of said perfumes include various perfumes of citrus, floral, green and woody notes.

Examples of the colors include tar dyes (e.g. azo Yellow No. 4, quinoline Yellow No. 203, etc.), uranine dyes (e.g. Yellow No. 202-1), triphenylmethane dyes (e.g. Blue No. 1, Green No. 3, etc.), and natural dyes (e.g. betanin, etc.) and so on.

Examples of soap and surfactants include, for example, basic salt of higher fatty acid (e.g. sodium salt, potassium salt, ammonium salt or triethanolamine salt of lauric acid, myristic acid, palmitic acid, stearic acid, oleic acid, and so on), salt of alkyl sulfuric acid ester (e.g. sodium lauryl sulfate, lauryl sulfate triethanolamine and so on), salt of alkyl ether sulfuric acid ester (e.g. sodium polyoxyethylene lauryl ether sulfate, polyoxyethylene lauryl ether sulfate triethanolamine and so on), N-acyl-sarcosinate (e.g. sodium N-lauroyl sarcosinate and so on), alkanolamide (e.g. lauric acid diethanolamide, palm oil fatty acid diethanolamide and so on), straight-chain alkyl benzenesulfonate (e.g. sodium laurylbenzenesulfonate and so on) and polyoxyethyleneglyceryl mono fatty acid ester (e.g. polyoxyethylene glyceryl stearate and so on), and so on.

Furthermore, preservatives such as p-hydroxybenzoic acid ester, which are generally contained in liquid soap or shampoo, may be dispensed, if necessary.

In formulating the bath preparation of the present invention, such as tablets, granules and so on, a binder can be employed.

Examples of such binder include crystalline cellulose, carboxymethylcellulose sodium, gelatin, starch, dextrin, methylcellulose, hydroxypropylmethylcellulose, sodium alginate, polyvinylpyrrolidone, gum trangacanth, and the like.

In dissolving the bath preparation of the invention in bath water, the concentration of ascorbic acid in the bath water may range from 10 to 500 ppm.

The bath preparation of the present invention has the effect that the ascorbic acid compound contained therein is not decomposed and oxidized to dehydroascorbic acid by residual free chlorine in the tap water.

The following experimental and working examples are further illustrative of the invention. In the following description, "part(s)" means "weight part(s)".

EXPERIMENTAL EXAMPLE 1

In 100 ml of purified water were dissolved 300 mg of sodium ascorbate and 50 mg of one of the reducing agents mentioned below. This aqueous solution containing sodium ascorbate was diluted with tap water to make 10 liters and warmed to 40° C. The solution was maintained at this temperature for 2 hours, after which the sodium ascorbate was assayed by high performance liquid chromatography (HPLC) under the following conditions.

HPLC conditions

Column: μ-Bondapak C18 (Waters Associates, U.S.A.), 3.9 mm×300 mm.
Column temperature: 40° C.
Eluent: [0.005M - sodium 1-heptanesulfonate+0.05M ammonium monohydrogen phosphate+0.1% acetic acid]:[methanol]=3:1.
Ditector: UV 270 nm The results in terms of % residual sodium ascorbate are shown in Table 1.

TABLE 1

| Reducing agent | % Residue of sodium ascorbate after 2 hrs at 40° C. |
| --- | --- |
| Control (not added) | 4.3% |
| Sodium thiosulfate | 94% |
| Sodium dithionite | 89% |
| L-cysteine hydrochloride | 82% |
| Glutathione | 80% |
| Propyl gallate | 50% |

Compared with the control run without addition of a reducing agent, the bath preparations containing a reducing agent according to the present invention were invariably stable without decomposition of sodium ascorbate.

EXPERIMENTAL EXAMPLE 2

In 100 ml of purified water were dissolved 5 g of ascorbic acid, 750 mg of one of the reducing agents mentioned below, 50 mg of a dye (Yellow No. 202-1) and 300 mg of a lemon-note perfume to give a liquid bath preparation. Ten milliliters of this bath preparation was diluted with tap water to make 12.5 liters and warmed to 40° C. The dilution was kept at this temperature for 2 hours and, then, its ascorbic acid content was determined by HPLC under the same conditions as Experimental Example 1. The results are shown in Table 2.

TABLE 2

| Reducing agent | % Residue of ascorbic acid after 2 hrs at 40° C. |
| --- | --- |
| Control (not added) | 5.1% |
| Sodium thiosulfate | 94.4% |
| L-cysteine hydrochloride | 62.0% |

Compared with the control run without addition of a reducing agent, the bath preparations containing sodium thiosulfate or L-cysteine hydrochloride were invariably stable in regard to ascorbic acid.

EXAMPLE 1

(Effervescent Tablets)

In a V-shaped blender (Tokuji Seikasho K.K. Japan), 25 parts of sodium sulfate, 50 parts of sodium bicarbonate, 4 parts of succinic acid, 17 parts of ascorbic acid, 3 parts of sodium thiosulfate, 1 part of a woody-note perfume, and ½ part of a dye (Yellow No. 202-1) were thoroughly blended. Then, using a compressing machine (Kikusui Seisakusho K.K., Japan), the mixture was compressed into tablets each with a diameter of 4.5 cm and a thickness of 1.2 cm and weighing 30 g to give bath tablets of the present invention.

EXAMPLE 2

(Effervescent Tablets)

In a V-shaped mixer, 37 parts of sodium bicarbonate, 36 parts of succinic acid, 20 parts of sodium ascorbate, 2 parts of sodium thiosulfate, 2 parts of crystalline cellulose, 2 parts of sodium benzoate, 1 part of a woody-note perfume and ½ part of a color (Yellow No. 202-1) were thoroughly blended. Then, using a compressing machine, the mixture was compressed into tablets each with a diameter of 4.5 cm and a thickness of 1.8 cm and weighing 50 g to give effervescent tablets of the present intention.

EXAMPLE 3

(Granular Bath Preparation)

Twenty parts of ascorbic acid, 24 parts of sodium sulfate and 4 parts of propyl gallate were blended together and granulated in the conventional manner to give granules (A) (particle diameter 300–1400μ). Separately, 50 parts of sodium bicarbonate, 1 parts of sodium carboxymethylcellulose, 1 part of a lemon-note perfume and ½ part of a color (Yellow No. 202-1) were mixed together and granulated in the conventional manner to give granules (B) (particle diameter 300–1400μ). The obtained granules (A) and (B) were blended to give a granular bath preparation of the invention.

EXAMPLE 4

(Liquid Preparation)

Twenty parts of sodium, ascorbaste, 5 parts of succinic acid, 3 parts of sodium thiosulfate, 1 part of a lemon-note perfume and ½ part of a color (Yellow No. 202-1) were dissolved in a sufficient quantity of water to make 100 parts of a liquid bath preparation according to the present invention.

EXAMPLE 5

(Effervescent Tablets)

To the mixture consisting of 10 parts of sodium bicarbonate, 9 parts of sodium carbonate, 4 parts of sodium thiosulfate and 14 parts of anhydrous lactose, a small amount of water was added. By a vertical granulator (Fuji Industry, Japan) the mixture was granulated and then dried to give granules A (particle diameter: 20 to 250μ).

To the mixture consisting of 34 parts of ascorbic acid, 5 parts of succinic acid and 14 parts of anhydrous lactose, a small amount of water was added. By the above granulator, the mixture was granulated and then dried to give granules B (particle diameter: 20 to 250μ).

In a V-shaped blender (Tokuju Seisakusho K.K., Japan), the granules A and B were blended. To the obtained mixture, 9 parts of fumaric acid, 1 part of a lemon-note perfume and ½ part of a color (Yellow No. 202-1) were added and blended. By Single-punch compressing machine(Kikusui Seisakusho K.K., Japan), the mixture was compressed into tablets each with a diameter of 4.5 cm and a thickness of 1.2 cm and weighing 30 g to give bath preparation of the present invention.

EXAMPLE 6

(Effervescent Tablets)

To the mixture consisting of 10 parts of sodium bicarbonate, 8 parts of sodium carbonate, 2 parts of sodium thiosulfate and 10 parts of anhydrous lactose, a small amount of water was added. By a vertical granulator, the mixture was granulated and then dried to give granules A (particle diameter: 20 to 250μ).

To the mixture consisting of 34 parts of ascorbic acid, 2 parts of L-cysteine hydrochloride, 15 parts of anhydrous sodium sulfate and 8 parts of anhydrous lactose, ½ part of water was added. By the above granulator, the mixture was granulated and then dried to give granules B (particle diameter: 20 to 250μ).

In a V-shaped blender, the granules A and B were blended. To the obtained mixture, 10 parts of adipic acid, 1 part of a woody-note perfume and a small amount of a color (Yellow No. 202-1) were added and blended. By a single-punch tablet machine, the mixture was compressed into tablets each with a diameter of 4.5 cm and a thickness of 1.2 cm and weighing 30 g to give a bath preparation of the present invention.

EXAMPLE 7

(Bubble Bath Preparation)

To 20 parts of water, 30 parts of sodium polyoxyethylene lauryl ether sulfate was added and mixed homogeneously. After 0.05 part of butyl paraben was dissolved in the mixture with heating, 3.5 parts of palm oil fatty acid polyoxyethyleneglyceryl and 0.5 palm oil fatty acid diethanolamide were added and mixed homogeneously to give an A group.

In 25 parts of water, 0.05 part of methyl paraben was dissolved with heating. After cooling the mixture to about ordinary temperature, 15 parts of sodium ascorbate, 1 part of sodium thiosulfate, 1.5 parts of sodium chloride and 0.5 part of citrus-note perfume were added to give an aqueous solution (B group).

The groups A and B were blended and then added in a sufficient quantity of water to make 100 parts of a bath preparation of the present invention, as a homogeneous and transparent liquid.

EXAMPLE 8

(Granular Bath Preparation)

Thirty parts of sodium sulfate, 10 parts of magnesium ascorbic acid-2-phosphate and 2 parts of sodium thiosulfate were blended together and granulated in the conventional manner to give granules (A) (particle diameter 200 to 1400μ).

Twenty-five parts of sodium hydrogen carbonate and 6 parts or borax, were blended together and granulated in the conventional manner to give granules (B) (particle diameter 200 to 1400μ).

Twenty parts of citric acid, 5 parts of sodium chloride, 2 parts of a lemon-note perfume and a suitable amount of a colon (Yellow No. 202-1) were mixed together and granules (C) (particle diameter 200 to 1400μ).

The obtained granules (A), (B) and (C) were blended to give a granular bath preparation of the invention.

What is claimed is:

1. In a bath preparation the combination of
   (a) at least one member selected from the group consisting of ascorbic acid, sodium ascorbate, and calcium ascorbate, and
   (b) at least one reducing agent selected from the group consisting of sodium dithionite, potassium dithionite, L-cysteine hydrochloride, glutathione and propyl gallate,
   the proportion of component (b) to component (a) being 0.02 to 2 parts by weight.

2. In a bath preparation the combination of claim 1, wherein the reducing agent is sodium dithionite or potassium dithionite.

3. In a bath preparation the combination of claim 1, wherein the reducing agent is propyl gallate.

* * * * *